(12) United States Patent
Hovhanessian et al.

(10) Patent No.: US 9,038,478 B2
(45) Date of Patent: May 26, 2015

(54) METHOD FOR DETERMINING THE FATIGUE CAPITAL OF A CABLE

(75) Inventors: Gilles Hovhanessian, Antony (FR); Alexandre Chaperon, Paris (FR); Erik Mellier, Viroflay (FR)

(73) Assignee: Soletanche Freyssinet, Rueil Malmaison (FR)

( * ) Notice: Subject to any disclaimer, the term of this patent is extended or adjusted under 35 U.S.C. 154(b) by 0 days.

(21) Appl. No.: 14/123,489

(22) PCT Filed: Jun. 4, 2012

(86) PCT No.: PCT/EP2012/060534
§ 371 (c)(1),
(2), (4) Date: Mar. 7, 2014

(87) PCT Pub. No.: WO2012/164104
PCT Pub. Date: Dec. 6, 2012

(65) Prior Publication Data
US 2014/0190268 A1    Jul. 10, 2014

(30) Foreign Application Priority Data

Jun. 3, 2011 (EP) .................................... 11305684

(51) Int. Cl.
G01N 3/32 (2006.01)
G01N 3/20 (2006.01)
G01D 1/16 (2006.01)
G01M 5/00 (2006.01)

(52) U.S. Cl.
CPC ............... *G01N 3/32* (2013.01); *G01M 5/0025* (2013.01)

(58) Field of Classification Search
USPC ............................................ 73/812, 849, 789
See application file for complete search history.

(56) References Cited

U.S. PATENT DOCUMENTS

2006/0288770 A1* 12/2006 Nowack ........................... 73/158
2011/0036148 A1* 2/2011 Stubler et al. ............... 73/40.5 R

OTHER PUBLICATIONS

Gilles Hovhanessian: "Health Monitoring of Cable Stayed Structures Experience and Implementation", Conference: 2006 IMAC-XXIV: Conference & Exposition on Structural Dynamics, Nov. 12, 2010, XP055010940, Retrieved from the Internet: URL:http://sem-proceedings.com/24i/sem.org-IMAC-XXIV-Conf-s17p02-Health-Monitoring-C able-Stayed-Structures-Experience-Implemen tation. pdf [retrieved on Nov. 1, 2011] section I, II, III, V, VII, figures 1-3.

(Continued)

*Primary Examiner* — Lisa Caputo
*Assistant Examiner* — Jamel Williams
(74) *Attorney, Agent, or Firm* — McKenna Long & Aldridge LLP

(57) ABSTRACT

The invention relates to a method for determining the fatigue capital of a cable supporting a civil engineering structure, the method including: a measuring step (S1, S2) during which the normal tensile stress in the cable and the bending stress in the cable are measured in a synchronized manner so as to obtain the compound stress in the cable; a counting step (S3) during which a count of the number of stress cycles, depending on the amplitude of the stress, is carried out from the measured compound stresses; and a step (S4) of assessing the fatigue capital of the cable during which the fatigue capital of the cable is determined by comparing the count, carried out in the counting step, with a pre-set Wohler curve for the cable.

20 Claims, 1 Drawing Sheet

(56) References Cited

OTHER PUBLICATIONS

D Siegert et al: "Fatigue of stay cables inside end fittings high frequencies of wind induced vibrations", Jul. 13, 2004, XP055011112, Retrieved from the Internet: URL:http://media.lcpc.fr/ext/pdf/pres/div_macoa/sources_articleoipeec.pdf [retrieved on Nov. 3, 2011], section 2.1-2.3.

M Poser et al: "Bending Fatigue Tests on Stays Cables", Jul. 13, 2008, XP055011117, Retrieved from the Internet: URL:http://posereng.com/downloads/BendingFatiguePaper2002.PDF [retrieved on Nov. 3, 2011], the whole document.

Li H et al: "Applications of optical fibre Bragg gratings sensing technology-based smart stay cables", Optics and Lasers in Engineering, Elsevier, vol. 47, No. 10, Oct. 1, 2009, pp. 1077-1084, XP026470030, ISSN: 0143-8166, DOI: 10.1016/J.OPTLASENG.2009.04.016 [retrieved on May 20, 2009], abstract, section 2., 3.

Jan Ming Ko: "Field vibration tests of bridge stay cables incorporated with magnetorheological (MR) dampers", Proceedings of SPIE, vol. 4696, Jan. 1, 2002, pp. 30-40, XP055011120, ISSN: 0277-786X, DOI: 10.1117/12.472567, abstract, figures 4,5.

* cited by examiner

METHOD FOR DETERMINING THE FATIGUE CAPITAL OF A CABLE

This Application is a 35 U.S.C. §371 National Stage Entry of International Application No. PCT/EP2012/060534, filed Jun. 4, 2012 and claims the benefit of European Application No. 11305684.0, filed Jun. 3, 2011, all of which are incorporated by reference in their entirety herein.

The present invention concerns a method for determining the fatigue capital of a cable supporting a civil engineering structure as well as a device for determining the fatigue capital of such a cable.

BACKGROUND

A great number of civil engineering structures are supported by cables, in particular, but not exclusively, cable-stayed bridges and suspension bridges.

These cables are generally anchored to the civil engineering structure by anchor means that are similar to an end-fitting, possibly imperfect. Consequently, the cables, in addition to being subject to longitudinal tensile forces, are subject to parasitic bending forces, which create local bending stresses.

The cables are subject to various types of loads, in particular, what are known as static and dynamic loads.

Static loads are generally due to slow changes, for example, changes in temperature or overall changes of the load on the civil engineering structure.

Dynamic loads correspond to more rapid changes, for example, wind gusts or the passage of a truck over the civil engineering structure.

The stresses that result from these loads, even if they are below the resistance of the cable, can lead to rupture of said cable if they are repeated too many times. In this case we speak of fatigue failure of the material constituting the cable.

There are calculation guidelines that can be used to verify that cable dimensions are compatible with the loads to which the structure is liable to be subjected during its lifetime.

Generally, these calculation guidelines consist, initially, in determining the fatigue capital, or the initial capital of the cable. Subsequently, we evaluate the loads the structure will be subjected to during its lifetime as well as the frequency of those loads. Finally, we make sure that those evaluated loads only partially consume the initial capital of the cable.

The cables are subject to fatigue, primarily in their anchorage zone, where fluctuations in tensile loads or axial stress are added to bending stress. Bending stress can be significant, for the cable experiences angular variations, as a result of which said cable is not perfectly aligned with its anchorage. The fluctuation of this anchorage angle due to movement of the structure, to cable vibration, or to the alteration of its catenary arc associated with variations in tensile load, result in bending stresses that are variable and significant.

While calculations can be used to evaluate the fatigue damage to cables and, thus, their lifespan during the design stage, these calculations are limited by the initial assumptions.

For example, in the case of a bridge, cable fatigue associated with automobile traffic on a bridge is based on estimates that can be exceeded over time.

Moreover, dynamic effects associated with the passage of convoys, especially truck convoys, are currently not fully taken into account during calculations. Finally, some dynamic effects, associated with the condition of the roadway, are simply not predictable.

Moreover, the dynamic effects of wind are hard to quantify. Vibrations, their amplitude and frequency of occurrence are largely unknown during the design of the system.

Therefore, it is useful to be able to follow the evolution of the initial fatigue capital of the cable supporting a structure during the life of said structure.

In this way, maintenance or upgrading activities can be planned in the event of the abnormally rapid consumption of fatigue capital or whenever it is nearly exhausted.

An object of the present invention is to provide a method for determining the fatigue capital of a cable supporting a civil engineering structure.

SUMMARY

Therefore, the invention proposes a method for determining the fatigue capital of a cable supporting a civil engineering structure, wherein the method comprises:
a measurement step during which the normal tensile force on the cable and the bending force on the cable are synchronously measured so as to obtain the compound force on the cable;
a counting step during which, based on the measured compound forces, a count of the number of stress cycles as a function of the amplitude of the force is realized;
a step involving evaluation of the fatigue capital of the cable during which the fatigue capital of the cable is determined by comparing the count carried out during the counting step with a Wöhler-type curve that has been previously determined for the cable.

Advantageously, the method according to the invention can be used to determine the actual load experienced by the cable and, by extrapolation, estimate the past and future load, and the evolution of the fatigue capital of said cable.

A method for determining the fatigue capital of a cable according to the invention can also include one or more of the optional characteristics below, considered individually or in any possible combination:
measurement of the normal tensile force on the cable is realized directly, for example, by means of a load cell; and/or
measurement of the normal tensile force on the cable is realized indirectly, for example, by the use of a strain gauge placed on the anchor, or by measuring the force on one among a plurality of cable strands, or by use of the vibrating chord method and measurement of the frequencies inherent in cable vibration; and/or
measurement of the bending force on the cable is realized directly; and/or
measurement of the bending force on the cable is realized from one or more strain gauges placed on or in the anchor or on the cable; and/or
measurement of the bending force on the cable is realized indirectly, for example, based on a measurement of cable movements in a plane intersecting its axis, for example, perpendicular to its axis, and at a known distance from the anchor; and/or
measurement of cable movement is realized in a shock absorber placed on the cable to dampen transverse vibrations; and/or
measurement of movement is obtained by accelerometric measurements integrated twice; and/or
measurement of movement is obtained by means of the velocities obtained by a geophone integrated once; and/or
tensile and/or bending measurements are realized at a frequency on the order of 1 Hz to 1 kHz; and/or the measurement step is realized during the shortest possible measurement period so it remains economical but is sufficiently long to be representative and enable a realistic extrapolation of loads before and after the measurement period, this duration typically being on the order of the week or month; and/or the measurement step is realized continuously from the time of cable installation so as to measure the tensile and bending forces on the cable from the time of its installation; and/or the counting step is realized by means of a type of counting known as "rainflow" counting; and/or the history or extrapolation of past loads is used to compare the fatigue actually experienced by the cable with the assumptions made at the time of construction; and/or extrapolations of future loads are used to estimate the capacity or lifetime of the cable with respect to fatigue; and/or the movement sensor used to measure bending is integrated in a shock absorber used to limit cable vibrations; and/or the movement sensor integrated in the shock absorber is also used to measure the cumulative travel of the shock absorber and track its aging.

The invention also concerns a device for determining the fatigue capital of a cable supporting a civil engineering structure, wherein the device has means for implementing a method according to the invention, that is, comprising:

means for measuring the overall tensile force experienced by the cable;

means for measuring the overall bending force experienced by the cable;

means for counting the number of stress cycles as a function of the amplitude of tensile and bending forces experienced by the cable; and means for comparing the counting carried out by the counting means with a Wöhler-type curve previously established for the cable.

A device according to the invention can also include one or more of the optional characteristics below, considered individually or in any possible combination:

alert means (16) for automatic notification whenever the cable's capacity or its residual lifespan are reduced below a predetermined threshold; and/or the anchoring device of the cable on the civil engineering structure comprises a shock absorber that integrates a sensor for measuring the cable's bending force.

BRIEF DESCRIPTION OF THE DRAWINGS

The invention will be easier to understand after reading the following description, which is provided solely as an example, and referring to the attached drawings, in which.

DESCRIPTION OF EMBODIMENTS

Figure 1:
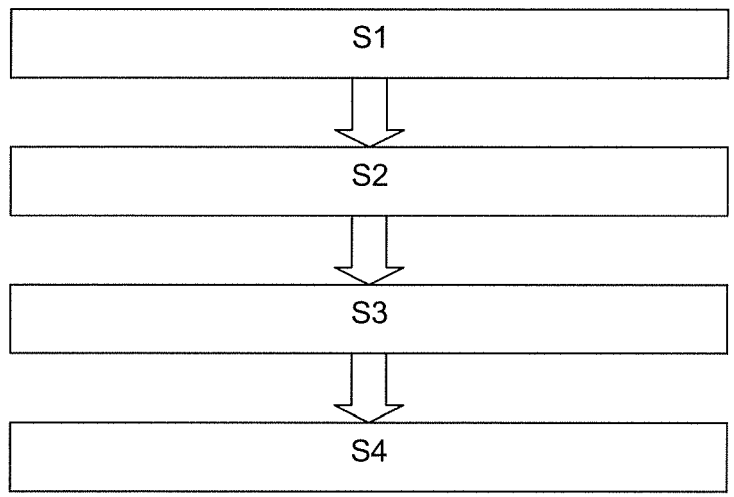
FIG. 1 illustrates the different steps of a method according to an embodiment of the invention.

For reasons of clarity, the different elements shown in the figures are not necessarily to scale.

The invention seeks to enable the determination of the fatigue capital of at least one cable supporting a civil engineering structure. The civil engineering structure may be of any kind, in particular, a suspension bridge or a cable-stayed bridge. According to an embodiment, a method according to the invention comprises:

a tensile measurement step, S1
a bending measurement step, S2
a counting step, S3, and
a step to determine the fatigue capital of the cable, S4.

During the steps involving tensile measurement, S1, and bending measurement, S2, the measurements are made in such a way that they estimate the stresses where the forces are greatest, that is, in general, in the anchorage zones of the cable of the civil engineering structure. Additionally, the tensile measurement steps, S1, and bending measurement steps, S2, are realized synchronously in order to obtain the compound force on the cable.

According to an embodiment of the invention, during the tensile measurement step, S1, measurement of the normal tensile force on the cable can be realized directly by any means known to the skilled practitioner. For example, measurement of the normal tensile force can be realized by means of a load cell. Here we call a "load cell" a sensor specifically designed to measure the tensile load on the cable or one of the strands of the cable. There are a large number of sensors of this type. Advantageously, this embodiment provides directly usable information.

According to another embodiment of the invention, during the tensile measurement step, S1, measurement of the normal tensile force on the cable can be realized indirectly by any means known to the skilled practitioner. For example, measurement of the normal tensile force can be realized by means of a strain gauge placed on the anchorage. Here, we call a "strain gauge" a sensor that can be used to measure the change in the deformation of the steel associated with a change in the load. These sensors are sometimes, erroneously, referred to as stress gauges, for knowledge of the modulus of steel can be used to calculate the local stress from the deformation ($\sigma = E\epsilon$). There are a large number of sensors of this kind, which operate on electrical or optical principles. An interpretation and possibly a calibration step may, in this case, be necessary to estimate the tensile load on the cable from measurements supplied by the sensors. This embodiment is, in general, used when direct measurement is not possible, for example, when it is not possible to install the sensor.

Another way to indirectly measure the normal tensile force in a multistrand cable that is stretched using a method of the isotension type, which ensures that the forces on the strands are similar (for example, as described in EP 0421862), can be based on measurement of the force on a strand.

Yet another way of indirectly measuring the normal tensile force on the cable can make use of the vibrating chord method and employ a measurement of the cable's inherent frequencies of vibration.

During the bending measurement step, the bending force on the cable is measured in the proximity of the anchorage of said cable on the structure, for example at the anchorage.

According to an embodiment of the invention, the bending measurement can be made by measuring the relative inclination of the cable with respect to its anchorage on the civil engineering structure.

According to an embodiment of the invention, measurement of the bending force on the cable can be realized directly by any means known to the skilled practitioner.

For example, based on one or more strain gauges placed on or in the anchorage or the cable. We could, for example, advantageously use the same type of gauge used for axial measurement.

According to an embodiment of the invention, measurement of the bending force on the cable can be realized directly by any means known to the skilled practitioner. For example, based on measurement of cable movements in a plane intersecting its axis, for example, perpendicular to its axis, and at a predetermined distance from the anchorage. Advantageously, this embodiment does not require access to the maximum bending zone, which is often difficult, nor the installation of sensors for direct measurement, which is often impossible at this location.

The overall bending force can be determined by means of a sensor that can be used to measure the angle made by the cable with its anchorage. This angle measurement can be used to determine, by calculation, the bending stresses experienced by the cable.

To measure the bending force on the cable, inclinometers can be used. According to an embodiment of the invention, a first inclinometer is arranged on the cable where it exits the anchorage to determine the absolute inclination of said cable.

A second inclinometer, arranged on the structure in the vicinity of the anchorage, is used to determine the absolute inclination of said structure. The difference in inclinations is used to determine the relative inclination of the cable in its anchorage, the anchorage being integral with the structure.

According to another embodiment, it is possible to determine the bending force at the anchorage by measuring the movement of the cable with respect to the structure at a certain distance from the anchorage.

Preferably, this distance is sufficiently large for the movements to be significant and measurable, and sufficiently small to be able to simplify the calculation by comparing the cable to a fixed-end beam subject to a force at its extremity. The typical order of magnitude is from 1 to 10 m.

Calculation of the bending force from the measured movement must be appropriate to the configuration of the cable and the anchorage (dimensions, presence of a deviator, etc.).

For example, for cables whose lower anchorage is situated on the deck of a bridge, the corresponding distance at the end of the cover tube is quite suitable.

On certain bridges, the end of the cover tube is equipped with a shock absorber. The movement sensor can then, advantageously, be incorporated in the shock absorber. In addition to allowing the bending force on the cable to be evaluated where it exits the anchorage, it can be used to track the cumulative travel of the shock absorber, a significant parameter for monitoring its aging and programming its maintenance. This measurement can be realized by movement sensors, or by a video capture combined with image analysis, or by any other means known to the skilled practitioner.

According to an embodiment of the invention, the tensile measurement, S1, and bending measurement, S2, steps can take place at frequencies greater than or equal to 1 Hz, for example, greater than or equal to 10 Hz, and less than or equal to 1 kHz, for example, less than or equal to 500 Hz, or even less than or equal to 100 Hz. In practice, a value of a few Hz (let's say 10 Hz for a "flexible" structure to 50 Hz for a "stiff" structure) is generally sufficient to measure the vibrations associated with the first normal modes of vibration.

However, it can be beneficial to oversample when measuring vibrations associated with traffic or to install digital filters and avoid aliasing phenomena.

Preferably, the measurement frequency is adjusted so that the greatest possible number of force changes on the cable can be taken into account and, in particular, any extreme values reached during each cycle.

The normal frequencies of vibration of the cable and the speed of convoys in the vicinity of the cable can be taken into account. Typically, about forty measurements are made per oscillation cycle and a measurement is taken approximately every 10 cm when a convoy is passing at maximum speed.

For example, for a convoy traveling at 100 km/h, that is, 100,000/3,600 m/s, with a measurement taken every 10 cm, the data are recorded at a frequency of 100,000/0.1/3,600=approximately 300 Hz.

The tensile measurement, S1, and bending measurement steps, S2, are realized during the shortest possible measurement period so they remain economical, but sufficiently long to be representative and enable a realistic extrapolation of loads before and after the measurement period. This duration is typically on the order of the week or month.

The method according to the invention also comprises a counting step during which, based on the measured compound stresses, a count of the stress cycle number as a function of the amplitude of the stress is realized.

According to an embodiment of the invention, the counting step is realized by means of a type of counting known as "rainflow" counting.

Rainflow counting is used to translate the stress load as a function of time into simple stress cycles characterized by a minimum stress and a maximum stress. This involves resolving the load by associating pairs of increasing minima and decreasing maxima. However, this association would entail the a posteriori analysis of the complete load as a function of time, and a complete history of the load would have to be maintained. To avoid storing this information, an algorithm associates pairs of minima and maxima to obtain partial cycles during loading.

The step in which the fatigue capital of the cable is determined can be used to determine the fatigue capital of the cable by comparing the count carried out during the counting step with a Wöhler-type curve that has been previously established for the cable.

The Wöhler curve defines a relation between the applied stress, σ, sigma, sometimes written S, and the number of cycles at failure, NR, in other words, the number of cycles for which we observe P % of failures. In practice, the Wöhler curve is generally given for a failure probability P=0.5.

Advantageously, the history or extrapolation of past forces can be compared with the actual fatigue experienced by the cable to verify the assumptions made when the structure was built.

Moreover, extrapolations of future loads can be used to estimate a capacity or a residual lifetime of the cable with respect to fatigue.

The invention concerns a device that can be used to determine the fatigue capital of a cable supporting a civil engineering structure.

Figure 2:
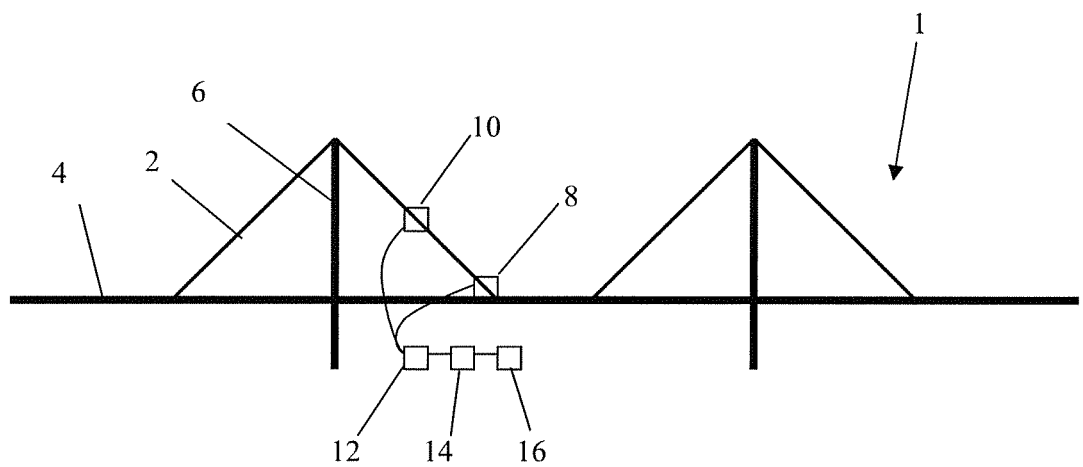
FIG. 2 is a schematic view of a cable-stayed bridge having a device according to the invention.

An example of a civil engineering structure supported by cables is shown in FIG. 2.

FIG. 2 is a schematic view of a cable-stayed bridge, 1. Cable-stayed bridge 1 comprises oblique cables, 2, connected to a tower, 6, and supporting the deck, 4.

The bridge represented in FIG. 2 is equipped with a device according to an embodiment of the invention.

Means for measuring the overall tensile force, 8, on the cable are disposed at the anchorage of cable 2 on deck 4.

Means for measuring the overall bending force, 10, on cable 2 are disposed along cable 2.

Means for measuring the overall tensile force 8 and bending force 10 are connected to a counting means, 12. Counting means 12 can be used to count the number of stress cycles as a function of the amplitude of tensile and bending forces experienced by the cable. Counting means can, for example, be a processor programmed to realize the counting.

According to the embodiment of FIG. 2, counting means 12 transmit to comparison means 14 the results of the counting performed. Comparison means 14 can be used to compare the counting carried out by the counting means with a Wöhler-type curve previously established for cable 2.

According to an embodiment, the device according to the invention can comprise alert means, 16, for signaling whenever the capacity of the cable or its residual lifetime is reduced below a predetermined threshold.

The invention is not limited to the embodiments described and should be interpreted in a non-limiting manner, and encompassing any equivalent embodiment.

The invention claimed is:

1. A method for determining a fatigue capital of a cable supporting a civil engineering structure, wherein the method comprises:
   a measurement step during which a normal tensile force on the cable and a bending force on the cable are synchronously measured so as to obtain a compound force on the cable;
   a counting step during which, based on the measured compound forces, a count of a stress cycle number as a function of an amplitude of the force is realized; and
   a step of evaluating the fatigue capital of the cable, during which the fatigue capital of the cable is determined by comparing the count carried out during the counting step with a Wöhler-type curve previously determined for the cable.

2. The method of claim 1, wherein the normal tensile force on the cable is measured directly.

3. The method of claim 1, wherein the normal tensile force on the cable is measured indirectly.

4. The method of claim 1, wherein measurement of the bending force on the cable is directly realized.

5. The method of claim 1, wherein measurement of the bending force on the cable is realized indirectly.

6. The method of claim 5, wherein the measurement of cable movements is realized in a shock absorber placed on the cable to dampen transverse vibrations.

7. The method of claim 1, wherein tensile and/or bending measurements are realized at a frequency on the order of 1 Hz to 1 kHz.

8. The method of claim 1, wherein the measurement step is not realized continuously from the moment of cable installation, and wherein the measured data are used to extrapolate from loads before and after the measurement period.

9. The method of claim 1, wherein the measurement step is realized continuously from the time of cable installation so as to measure the tensile and bending forces on the cable from the time of its installation.

10. The method of claim 1, wherein the counting step is realized by means of rainflow counting.

11. The method of claim 1, wherein history or extrapolation of past loads is used to compare the fatigue actually experienced by the cable with the assumptions made at the time of construction.

12. The method of claim 1, wherein extrapolations of future loads are used to estimate a capacity or residual lifetime of the cable with respect to fatigue.

13. A device for determining the fatigue capital of a cable supporting a civil engineering structure, the device comprising:
   means for measuring an overall tensile force on the cable;
   means for measuring an overall bending force on the cable;
   means for counting a number of stress cycles as a function of an amplitude of tensile and bending forces experienced by the cable; and
   means for comparing the counting carried out by the counting means with a Wöhler-type curve previously established for the cable.

14. The device of claim 13, further comprising alert means for automatic notification whenever a capacity or residual lifespan of the cable is reduced below a predetermined threshold.

15. The device of claim 13, wherein the anchoring device of the cable on the civil engineering structure comprises a shock absorber that integrates a sensor for measuring the cable's bending force.

16. The method of claim 2, wherein the normal tensile force on the cable is measured using a load cell.

17. The method of claim 3, wherein the normal tensile force on the cable is measured using a strain gauge placed on the anchor or on the cable.

18. The method of claim 3, wherein the normal tensile force on the cable is measured by measuring a force on one of a plurality of strands of the cable.

19. The method of claim 3, wherein the normal tensile force on the cable is measured by a vibrating chord method and using measurement of normal frequencies of vibration of the cable.

20. The method of claim 5, wherein measurement of the bending force on the cable is based on a measurement of cable movements in a plane intersecting an axis of said cable and at a known distance from an anchorage of said cable.

* * * * *